US006051260A

United States Patent [19]
Liska et al.

[11] Patent Number: 6,051,260
[45] Date of Patent: Apr. 18, 2000

[54] MEDICAL FOOD COMPOSITION OF REDUCED ALLERGENICITY, ESPECIALLY ADAPTED FOR IMPROVING GUT MUCOSAL INTEGRITY

[75] Inventors: De Ann Liska, Gig Harbor; Margaret King, Puyallup; Darrell Medcalf, Gig Harbor; De Brian Peterson, Tacoma; Jeffrey Bland, Fox Island, all of Wash.

[73] Assignee: Healthcomm International, Inc., Gig Harbor, Wash.

[21] Appl. No.: 09/056,734

[22] Filed: Apr. 7, 1998

[51] Int. Cl.$^7$ .......................... A61K 33/06; A61K 31/01; A61K 31/315; A61K 38/02

[52] U.S. Cl. .......................... 424/602; 424/51; 424/195.1; 424/655; 424/614; 426/2; 426/542; 426/549; 426/590; 426/598; 426/599; 514/2

[58] Field of Search .................................. 424/602, 655, 424/195.1, 614, 682; 426/2, 542, 549, 590, 598, 599, 51; 514/2

[56] References Cited

U.S. PATENT DOCUMENTS

| | | | |
|---|---|---|---|
| 4,810,506 | 3/1989 | Lewis et al. | 426/28 |
| 5,444,054 | 8/1995 | Garleb et al. | 514/54 |
| 5,629,023 | 5/1997 | Bland | 424/655 |
| 5,637,324 | 6/1997 | Bland | 424/655 |
| 5,661,123 | 8/1997 | Stalker et al. | 514/2 |
| 5,702,745 | 12/1997 | Yang et al. | 426/242 |

OTHER PUBLICATIONS

UltraClear Sustain, Trademark Registration Information, 1994.

UltraClear Patient Information Packet, 1998.

Bhattacharya, K. R., "Parboiling of Rice", Rice: Chemistry and Technology,(1972), Bienvenido O. J, Ed, St. Paul, MN:The Amer. Ass. of Cereal Chemists, Inc., p. 289–348.

Abbas, Abul K. et al., *Cellular and Molecular Immunology*, 2nd Ed., (1994), Philadelphia, MA: W.B. Saunders Company, p. 55–64.

P. G. Lunn, et al., Intestinal permeability, mucosal injury, and growth faltering in Gambian infants, *The Lancet*, vol. 338, Oct. 12, 1991, pp. 907–910.

Christine A. Northrop, et al., Automated enzymatic assays for the determination of intestinal permeability probes in urine. 1. Lactulose and lactose, *Clinica Chimica Acta*, 187, (1990), pp. 79–88.

The AJS Company, Fructooligosaccharide Information Package, *ZeaGen Inc.*, Broomfield, CO., Mar., 1992, pp. 1–18.

Tomotari Mitsuoka, et al., Effect of fructo–oligosaccharides on intestinal microflora, *Die Nahrung*, vol. 31 (1987) 5–6, pp. 427–436.

J. Edelman, et al., The Mechanism of Fructosan Metabolism in Higher Plants as Exemplified in Helianthus Tuberosus, *New Phytol.*, (1968) 67, pp. 517–531.

Marie–Anne Levrat, High Propionic Acid Fermentations and Mineral Accumulation in the Cecum of Rats Adapted to Different Levels of Inulin, *American Institute of Nutrition*, 1991, pp. 1730–1737.

Murphy, M.S et al., "Active and Passive Sugar Absorption in Pancreatic Insufficiency", *Journal of Pediatric Gastroenterology and Nutrition*, (1989), New York: Raven Press Ltd., 3:189–194.

Cordle CT. "Control of Food Allergies Using Protein Hydrolysates", *Good Tech*, (1994) Oct.: 72–76.

*Primary Examiner*—Jose' C. Dees
*Assistant Examiner*—Shahnam Sharareh
*Attorney, Agent, or Firm*—Klein & Szekeres, LLP

[57] ABSTRACT

Parboiled rice flour is used in lieu of other grain flour in medical foods to minimize antigenicity of the medical food product.

16 Claims, No Drawings

MEDICAL FOOD COMPOSITION OF REDUCED ALLERGENICITY, ESPECIALLY ADAPTED FOR IMPROVING GUT MUCOSAL INTEGRITY

BACKGROUND OF THE INVENTION

1. Field of the Invention

The present invention is in the field of medical foods and in the field of utilizing medical foods to reduce or minimize allergic reactions in individuals while under treatment by medical foods. More particularly, the present invention is directed to use of parboiled rice products in medical foods to reduce allergenicity of the medical food. Still more particularly the present invention is directed to a medical food composition which, when taken as a meal supplement improves the integrity of gastrointestinal mucosa and does so with minimal potential for allergic reaction.

2. Brief Description of the Prior Art

Parboiled rice is rice that has been precooked within the hull, and this food product has been known and served for a long time as an important staple of diet in many parts of the world. Chapter 8 titled "Parboiling of Rice" by K. R. Bhattacharya of the book "Rice: Chemistry and Technology", edited by Bienvenido O. Juliano and published by the American Association of Cereal Chemists Inc. St. Paul, Minn., USA, 2nd edition 1985, describes in detail the traditional as well as the modern technology for parboiling of rice and mentions the public health implications of using this product as a staple of diet in large parts of Southern Asia. For example, it was noticed primarily in Southeastern Asia during the early part of this century is that persons who consumed milled parboiled rice as the main staple of their diet tended to be free of the debilitating vitamin deficiency disease called beriberi, whereas persons whose diet mainly consisted of milled raw rice tended to suffer from this disease.

To this date and to the present inventors' best knowledge there has been no description in the prior art of the presently discovered phenomenon of this invention, namely that food products containing parboiled rice, or parboiled rice flour tend to be significantly less allergy inducing than similar products comprising other cereal, and particularly non-parboiled rice products. In this regard it is noted that whereas rice and rice products are not generally known as highly allergenic, rice-associated allergy does occur, and it occurs more frequently in those individuals who continually eat rice products or are exposed to rice pollens. For example, in Japan rice-associated allergy has become a significant problem, and rice ranks second only to eggs as the most common allergen in the Japanese diet. One aspect of the present invention is the use of parboiled rice products in medical foods to eliminate or reduce the likelihood of allergic reactions in persons who are likely to suffer an allergic reaction to rice containing or other cereal products.

Another important aspect of the background pertinent to the present invention, especially as it is presently best utilized in a medical food composition, is in the treatment of individuals suffering from certain gastrointestinal disorders. More particularly, it is well known that over 12% of adult persons in the Western World, including the United States of America, have mild to moderate gastrointestinal symptoms including altered patterns of fecal evacuation, intestinal bloating or cramping after meals, flatulence, gut pain after eating, and altered gut mucosal permeability associated with inflammatory joint disease. Many of these problems are due to altered intestinal flora, to allergic manifestations related to secretory IgA of the intestinal tract and enterometabolic toxicity reactions. All of these conditions are exacerbated by foods that have allergenic potential and by poor gut mucosal integrity/leaky gut.

Due to these abnormalities significant increases in the passive absorption of toxic substances from the bowel into the portal blood supply can occur. This in turn puts a demand on hepatic detoxification systems resulting in alteration of Phase I cytochrome P450 enzymes and Phase II conjugating enzyme systems.

Altered gut flora can also result in the production of bacterial endotoxins which in turn influence gut permeability and hepatic detoxifying enzyme systems.

The cumulative effect from direct toxicity upon the gastrointestinal mucosa from alcohol, drugs or chemicals coupled with the influence of allergy-producing dietary proteins such as gluten from wheat and casein from milk products and the release of endotoxic lipopolysaccharides or HLA-B-27 like antigens from bacteria increases gut mucosal permeability and thus increases demand upon hepatic detoxification processes. The increase in Kupffer cell activity of the liver due to these exposures can also contribute to inflammatory processes at remote sites of the body (i.e. inflammatory joint disease).

The foregoing problems constitute a series of health concerns which are being more frequently recognized to be related to altered gut permeability. The burden on the hepatic detoxification mechanism by exposure to endo and exo toxins as a consequence of a permeable gut also is known to cause the release of oxidants such as superoxide, hydroxyl radical, hydrogen peroxide and singlet oxygen. These in turn have their own deleterious effects upon the nervous, immune, endocrine, cardiovascular, and gastrointestinal systems.

Until relatively recently, that is until a few years ago, there was no nutritional product, dietary composition or medical food which has been demonstrated to favorably influence the course of these processes. Then, approximately 5 years ago a medical food composition appeared on the market under the ULTRACLEAR SUSTAIN® trade name, which is reasonably effective for the treatment of the above-noted conditions, principally for the treatment of leaky gut and related syndromes. Because the preferred embodiment of the present invention is a significantly less allergenic improvement of the above-noted medical food sold in the United States under the ULTRACLEAR SUSTAIN® trade name, the following description of certain components is pertinent as background to the present invention as well.

Fructooligosaccharides are carbohydrate compounds available from natural sources or from fermentation processes where a glucopyranose moiety is coupled with a glycosidic bond to two or more fructofuranose moieties. Inulin is a naturally occurring carbohydrate available from a variety of plant sources, where a glucopyranose moiety is coupled with a glycosidic bond to several fructofuranose moieties; the line of distinction between fructooligosaccharides and inulin is generally drawn such that when the molecule contains 4 or less fructose moieties it is classified as a fructooligosaccharide, and when it contains more than 4 fructose moieties then it is known as inulin. Nevertheless, fructooligosaccharides and inulin are considered distinct chemical entities.

It has been known in the prior art that fructooligosaccharides and inulin are largely unaffected in the stomach and small intestine of humans and numerous other mammalian species, and that these compounds provide a suitable source of nutrition to certain beneficial bacteria such as Bifidobacteria which are part of the intestinal flora of humans and other mammalian species. The following technical descriptions and scientific publications describe or are related to inulin, fructooligosaccharides and/or their effect in the mammalian digestive system and gastrointestinal flora:

P. G. Lunn, et al., Intestinal permeability, mucosal injury, and growth faltering in Gambian infants, *The Lancet,* Vol. 338, Oct. 12, 1991, pages 907–910;

Christine A. Northrop, et al., Automated enzymatic assays for the determination of intestinal permeability probes in urine. 1. Lactulose 9 and lactose, *Clinica Chimica Acta,* 187, (1990), pages 79–88;

Zoltan Gregus, et al., Effect of Glutathione Depletion on Sulfate Activation and Sulfate Ester Formation in Rats, *Biochemical Pharmacology,* Vol. 37, No. 22, pp 4307–4312, 1988;

The AJS Company, Fructooligosaccharide Information Package, *ZeaGen Inc.,* Broomfield, CO., March, 1992, pgs. 1–18;

Tomotari Mitsuoka, et al., Effect of fructo-oligosaccharides on intestinal microflora, *Die Nahrung,* Vol. 31 (1987) 5–6, pgs. 427–436;

Peter J. Perna, Fructooligosaccharides (FOS) An all Natural Food Which Promotes Bifidobacteria and Lactobacillus, *ZeaGen, Inc.,* Broomfield, CO;

J. Edelman, et al., The Mechanism of Fructosan Metabolism in Higher Plants as Exemplified in Helianthus Tuberosus, *New Phytol.,* (1968) 67, pgs. 517–531;

Marie-Anne Levrat, High Propionic Acid Fermentations and Mineral Accumulation in the Cecum of Rats Adapted to Different Levels of Inulin, *American Institute of Nutrition,* 1991, pgs. 1730–1737;

The present invention pertains to the use of parboiled rice or parboiled rice flour in medical foods to reduce or eliminate the allergenic potential of such foods. The below described preferred embodiment of the invention is a medical food, incorporating inulin and fructooligosaccharides as well as parboiled rice flour, which demonstrably improves gastrointestinal permeability, results in improved hepatic detoxification and reduced oxidative stress and has very low allergenic potential.

OBJECTS AND SUMMARY OF THE INVENTION

It is an object of the present invention to provide a medical food composition, which in addition to being effective for its intended purpose includes a grain flour ingredient that has very low allergenic potential.

It is another object of the present invention to provide a medical food composition which results in improved gastrointestinal function through its positive impact on gastrointestinal mucosal integrity.

It is still another object of the present invention to provide a medical food composition and method for its use that reduces gastrointestinal inflammation due to food allergy.

Broadly speaking, the foregoing and other objects and advantages are attained by providing and administering to a human being a medical food composition which is effective for its intended nutritional or therapeutic purpose and which, in order to minimize allergic response in individuals susceptible to allergy induced by consumption of rice or rice products, contains rice flour or other rice products from parboiled rice.

In another aspect the objects and advantages of the invention are attained by administering on a daily basis to a human being for the purpose of improving gastrointestinal mucosal integrity, and for reduced gastrointestinal inflammation due to food allergic response, a medical food composition comprising:

approximately 38.3 to 46.8 percent by weight of rice protein concentrate which contains approximately 48 to 58 percent by weight of protein, or an equivalent gluten-free or substantially gluten-free grain protein concentrate;

approximately 14.2 to 21.2 percent by weight of parboiled rice flour;

approximately 16.00 to 24 percent by weight of rice syrup solids which contain approximately 70 to 90 percent by weight of high molecular weight dextran, or equivalent gluten-free or substantially gluten-free grain syrup solids;

approximately 1.2 to 1.8 percent by weight of medium chain triglycerides;

approximately 2.7 to 4.0 percent by weight of fructooligosaccharides;

approximately 1.9 to 2.8 percent by weight of inulin;

approximately 0.70 to 1.0 percent by weight of L-glutamine;

approximately 0.17 to 0.25 percent by weight of calcium pantothenate or an equivalent nutritionally acceptable source of pantothenic acid;

approximately 0.05 to 0.08 percent by weight of zinc picolinate, or an equivalent nutritionally acceptable source of zinc;

approximately 0.18 to 0.26 percent by weight of ascorbic acid, or an equivalent nutritionally acceptable form of Vitamin C;

approximately 0.05 to 0.075 percent by weight of d-alpha tocopheryl acetate, or an equivalent nutritionally acceptable form of Vitamin E.

DETAILED DESCRIPTION OF THE INVENTION

In accordance with the present invention parboiled rice or parboiled rice flour is used instead of rice or other grain flour in a medical food composition that is administered to a patient as a food supplement for any number of nutritional or therapeutic purposes. Unexpectedly and surprisingly it has been discovered in accordance with the present invention that parboiled rice and flour obtained from parboiled rice are significantly less allergenic than common (not parboiled) rice or rice flour obtained from non-parboiled rice.

In the below described example parboiled rice flour is used instead of common (non-parboiled) rice flour in a medical food composition that is administered to a patient as a food supplement approximately twice a day, for the purpose of improving gastrointestinal function by improving gastrointestinal mucosal integrity, and colonic flora, which results in elimination or improvement in the condition termed "leaky gut syndrome". The medical food composition of this example is also administered for the purpose of reducing endotoxin production, which then results in improved hepatic detoxification capability and reduced oxidative stress. Use of parboiled rice flour instead of common rice flour or instead of other grain flour significantly improves the composition because the composition with parboiled rice flour significantly reduces the risk of allergic reactions among persons who are treated with the composition.

The medical food composition of the herein described example is not designed for causing weight loss, although moderate weight loss may be experienced by individuals taking the composition as a food supplement, particularly if the composition is taken as a supplement to a substantially vegetarian diet of the type recommended in conjunction with the present composition.

The exemplary composition of the present invention includes approximately 38.3 to 46.8 percent by weight of rice protein concentrate which contains approximately 48 to 58 percent by weight of protein. An important characteristic of rice protein concentrate is that it is free of the protein gluten which is known to cause allergic reactions in many individuals. Instead of rice protein concentrate, other gluten-free or substantially gluten-free grain protein concentrate can also be used in equivalent amounts. Quinoa grain (a grain grown originally in the highlands of Peru) concentrate serves as an example for such a substantially gluten-free grain protein concentrate. The preferred embodiment of the dietary food composition of the present invention contains approximately 42.5 percent by weight of rice protein concentrate. Here and elsewhere in this application unless it is otherwise stated, all percentages are by weight. The rice protein concentrate is derived from white rice and may be fortified with certain amino acids, to wit: L-lysine, L-threonine and L-cysteine, although fortification with amino acids is not essential for the present invention.

The dietary or medical food composition of the present invention includes approximately 14.2 to 21.2 percent by weight of parboiled rice flour. The parboiled rice flour is preferably obtained from long grain rice. Again, a characteristic of rice flour is that it is generally free of gluten and gluten is known to be a substance that is likely to cause allergic reactions or symptoms among a substantial number of individuals. In other words gluten is a known allergen. However, as it is described in detail below in connection with the experiments that demonstrate the advantage of using parboiled rice flour instead of common (non-parboiled) rice flour, parboiled rice flour is even significantly less allergenic than common rice flour. This discovery is believed to be entirely novel and surprising especially in view of the fact that parboiled rice and rice flour obtained from parboiled rice have been known in the nutritional arts for a long time. The preferred embodiment of the dietary composition contains approximately 17.7 percent by weight of parboiled rice flour.

As is known in the nutritional and related art and trade, parboiled rice can be obtained in accordance with well known procedures such as the ones described in the above-cited book, Chapter 8 titled "Parboiling of Rice" by K R. Bhattacharya "Rice: Chemistry and Technology", edited by Bienvenido O. Juliano and published by the American Association of Cereal Chemists Inc. St. Paul, Minn., USA, 2nd edition 1985, which is incorporated herein by reference. Parboiled rice, and parboiled rice flour are also well known to be widely available commercially. A presently preferred source for the parboiled rice in the herein described exemplary composition is Comet Rice Company of Los Angeles, California.

The dietary or medical food composition of the present example includes approximately 16 to 24 percent by weight of rice syrup solids which contain approximately 70 to 90 percent by weight of high molecular weight dextran. This type of rice syrup solids is commercially available and is known in the trade as "Ultra High Maltose" (UHM) rice syrup solids. Equivalent gluten-free or substantially gluten-free grain syrup solids containing an equivalent amount of high molecular weight dextran, such as quinoa grain syrup solids can also be incorporated in this exemplary composition of the invention instead of the rice syrup solids. The preferred embodiment of the dietary composition contains approximately 20.00 percent by weight of rice syrup solids.

The dietary or medical food composition of the herein described example includes approximately 1.2 to 1.8 percent by weight of medium chain triglycerides. Medium chain triglycerides are defined as triglycerides which have fatty acid moieties having 8 to 14 carbon atoms. A suitable source for these fatty acid triglycerides is, for example, the oil derived from coconuts, and related tropical oils. In this regard it should be noted that whereas coconut oil is high in saturated long chain fatty acids, and is therefore considered undesirable because it promotes formation of cholesterol, the medium chain triglycerides derived from coconut oil do not give rise to cholesterol. The preferred embodiment of the dietary composition contains approximately 1.50 percent by weight of medium chain triglycerides.

The exemplary dietary or medical food composition of the present invention includes approximately 2.7 to 4.0 percent by weight of fructooligosaccharides. As is known in the art, fructooligosaccharides are carbohydrates wherein a glucopyranose moiety is coupled by a glycosidic bond to 2 to 4 fructofuranose moieties. As is known further, fructooligosaccharides are widely distributed in the plant world, and are present in significant quantities for example in onions, chicory and jerusalem artichokes, although presently preferred sources for the fructooligosaccharides used in the herein described composition do not include jerusalem artichokes.

Chemical structures of common fructooligosaccharides known as 1-kestose (1 glucose and 2 fructose units), nystose (1 glucose and 3 fructose units) and 1F-B-fructofuranosyl nystose (1 glucose and 4 fructose units) are shown below.

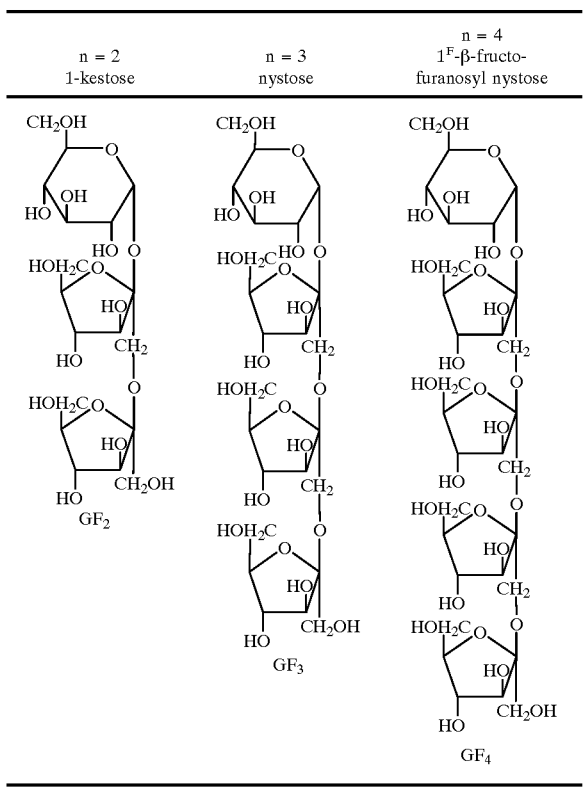

As noted above, jerusalem artichoke flour is a commercially feasible source of fructooligosaccharides, and can be used, although presently is not preferred, as a source of these components (as well as of inulin) in the herein described exemplary dietary composition. Other commercially feasible sources of fructooligosaccharides are products available from RhÔne-Poulenc (Cranbury, N.J.), known under the trade name RAFTILOSE P95®, and Imperial-Suiker Unie (Sugar Land, Tex.) known under the trade name FRUTAFIT®. These products are manufactured by a hot water extraction process of chicory root followed by a partial enzymatic hydrolysis. The preferred embodiment of the exemplary dietary composition of the present invention contains approximately 3.37 percent by weight of fructooligosaccharides, which are presently preferably obtained in the form of the RAFTILOSE P95® and FRUTAFIT® products.

Another ingredient of the exemplary dietary or medical food composition of the present invention which contains fructose is inulin, present in the composition in the range of approximately 1.9 to 2.8 percent by weight. As noted above, inulin is the common and joint name for certain carbohydrate molecules where one glucopyranosyl unit is coupled to several fructose units in varying degrees of polymerization (DP); with the lower limit being generally recognized as 5 fructose units, in the sense that with only 4 fructose units the molecule is considered a fructooligosaccharide not inulin. The lower limit of 5 fructose moieties in the above sense is also adopted here for the purposes of the present description. The upper limit for inulin is usually considered a DP of 50, which is also adopted for the present description.

As is known, various plant species including chicory contain inulin with various average degree of polymerization. For example, inulin obtained from chicory has an average DP of 9, and inulin from dahlia plants has an average DP of 30.

Although, as is known and is apparent from the foregoing, inulin and fructooligosaccharides are chemically related, they have different properties and in accordance with the present invention they form two separate and essential components of the herein described dietary composition. The preferred embodiment of the composition contains approximately 2.37 percent by weight of inulin obtained from the same sources as described above for fructooligosaccharides.

The exemplary dietary composition of the present invention also contains approximately 0.70 to 1.0 percent by weight of L-glutamine; approximately 0.17 to 0.25 percent by weight of calcium pantothenate, or an equivalent amount of nutritionally acceptable source of pantothenic acid; approximately 0.05 to 0.08 percent by weight of zinc picolinate, or an equivalent nutritionally acceptable source of zinc; approximately 0.18 to 0.26 percent by weight of ascorbic acid, or an equivalent nutritionally acceptable form of Vitamin C; and approximately 0.05 to 0.075 percent by weight of d-alpha tocopheryl acetate or an equivalent nutritionally acceptable form of Vitamin E. The preferred embodiment has approximately 0.86 percent L-glutamine, 0.20 percent calcium pantothenate, and 0.07 percent zinc picolinate, 0.22 percent ascorbic acid and 0.06 percent d-alpha tocopheryl acetate.

The above described components of the dietary composition or medical food of the present invention are considered essential, in the sense that the unique combination of these components results in a composition, which when used regularly as a food supplement for a time period of approximately 7 or more days, preferably for four to ten weeks, results in clinically measurable improvement in the intestinal mucosa of individuals suffering from "leaky gut" syndrome and related gastrointestinal disturbances and conditions such as dysbiosis, dyspepsia, enterometabolic disorders, certain food allergies and inflammatory bowel disorders.

In addition to the foregoing essential ingredients or components, the exemplary dietary composition of the present invention may also contain the following components which, although not essential, improve the performance of the composition particularly in the sense that they compliment the overall diet of the person who consumes the food supplement of the intention and provide reasonable assurance that the overall diet is not deficient in vitamins, minerals and other necessary components.

Thus, the dietary composition or medical food of the present example of the invention optionally contains the components listed below in a TABLE 1, indicating the preferable range of each component and also its actual percentage (by weight) in the preferred embodiment.

It should be understood in connection with the above-listed optional components or ingredients, that these nutritionally acceptable equivalents of these ingredients can also be used optionally, in equivalent quantities. Specifically, canola oil can be substituted with nutritionally equivalent oils, such as flaxseed oil. Calcium citrate can be substituted with a nutritionally acceptable source of calcium providing an equivalent amount of calcium ions. Instead of vanilla flavor, other flavors (approved by the requisite regulatory agency such as the Food and Drug Administration in the USA) can be used.

| OPTIONAL COMPONENTS | % IN PREFERRED EMBODIMENT | PREFERRED RANGE % |
|---|---|---|
| Canola Oil | 4.0000 | 3.2–4.8 |
| Vanilla Flavor | 1.5000 | 1.2–1.8 |
| Potassium Phosphate, Dibasic | 0.9000 | 0.72–1.08 |
| Beta-Carotene CWS 1% | 0.3433 | 0.275–0.412 |
| Calcium Citrate | 1.6349 | 1.3–1.96 |
| Magnesium Citrate | 1.2875 | 1.03–1.55 |
| Ferrous Fumarate | 0.0188 | 0.0150–0.0226 |
| Niacinamide | 0.0134 | 0.0107–0.016 |
| Molybdenum Amino Acid Chelate (Mo = 5%) | 0.0017 | 0.0014–0.002 |
| Manganese Gluconate | 0.0301 | 0.0241–0.0361 |
| Copper Gluconate | 0.0061 | 0.0049–0.0073 |
| Vitamin A (500,000 IU/gram) | 0.0100 | 0.008–0.012 |
| Pyridoxine Hydrochloride | 0.0016 | 0.001–0.002 |
| Riboflavin | 0.0011 | 0.0009–0.0013 |
| Thiamin Hydrochloride | 0.0010 | 0.0008–0.0012 |
| Vitamin D (100,000 IU/gram) | 0.0020 | 0.0016–0.0024 |
| Folic Acid | 0.0003 | 0.00024–0.00036 |
| Biotin (1% dilution) | 0.0201 | 0.016–0.024 |
| Vitamin K (1% dilution) | 0.01600 | 0.0128–0.0192 |
| Dicalcium Phosphate (Anhydrous) | 0.2074 | 0.1659–0.25 |
| L-Glutathione | 0.0086 | 0.007–0.01 |
| L-Cysteine HCl | 0.0112 | 0.009–0.0134 |
| L-Lysine HCl | 0.0751 | 0.06–0.09 |
| L-Threonine | 0.0601 | 0.05–0.07 |
| N-Acetylcysteine | 0.0086 | 0.007–0.01 |
| Selenomethionine (Se = 0.5%) | 0.0172 | 0.0138–0.0206 |
| Chromium Polynicotinate (Cr = 0.2%) | 0.0644 | 0.0515–0.0773 |
| Cyanocobalamin (0.1% dilution) | 0.0040 | 0.0032–0.0048 |

Magnesium citrate can be substituted with a nutritionally acceptable alternative source of magnesium. Dibasic potassium phosphate and dicalcium phosphate act as a buffer, and in case of the latter also as a source of calcium, and can be substituted with a nutritionally acceptable alternative buffer having the same buffering capacity. The vitamins or vitamin precursors β-carotene, vitamin A, vitamin D, can be provided in several forms, as applicable, and a person having ordinary skill in the art would readily know how to make such a substitution in light of the information provided above. For example the β-carotene CWS 1% solution which is listed in TABLE 1 of the preferred example is equivalent to approximately 0.0025 to 0.004 percent by weight of B-carotene in the composition. Chromium polynicotinate commercially available as ChromeMate GFT®, selenomethionine, manganese gluconate, ferrous fumarate, copper gluconate and molybdenum histidinate chelate are well known nutritionally acceptable sources for the elements chromium, selenium, manganese, iron, copper, and molybdenum, respectively and can be replaced by other nutritionally acceptable sources of the respective elements, in equivalent amounts. The chromium polynicotinate product specifically indicated in TABLE 1 is substantially equivalent to approximately 0.00010 to 0.00016 percent by weight of chromium in the composition. The selenomethionine product incorporated in the preferred example as shown in TABLE 1 is substantially equivalent in selenium content to approximately 0.00006 to 0.00010 percent by weight of selenium. The biotin solution incorporated in the preferred example is substantially equivalent to approximately 0.0001 to 0.0003 percent by weight of biotin. The molybdenum amino acid chelate product included in the preferred embodiment is substantially equivalent to approximately 0.00007 to 0.00010 percent by weight of molybdenum.

The exemplary composition of the present invention is prepared by intimately mixing the several ingredients which usually are in powder, or crystalline solid form. With regard to the fructooligosaccharides and inulin ingredients the following is noted. In the presently preferred embodiment the sources of inulin and fructooligosaccharides are chicory. The RAFFILOSE® and FRUTAFIT® products are included in the mixture in an amount calculated to bring the total amount of fructooligosaccharides and inulin to be the desired percentage, or to be within the desired range.

The medical food or dietary composition of the present example is a powdery substance. A 60-gram portion of the preferred embodiment provides approximately 220 kilocalories (Kcal). In accordance with the example the dietary food composition is to be taken preferably twice daily, each time in a 60-gram portion, as a meal supplement. The portion can be admixed with water, or fruit juice, as desired. Clinically measurable improvement, as measured by certain tests described below, can usually be observed after a person has taken the dietary food supplement for approximately one to two weeks.

Although this is not necessary, it is recommended that the dietary composition of the present example be taken in conjunction with a diet that is relatively free of allergy producing substances and is preferably vegetarian. A suggested meal schedule for one week duration is described below, as the recommended best mode for utilizing the dietary composition of the example:

| Week 1 | |
|---|---|
| Breakfast | approx. 60 g of the composition mixed in water |
| | ½ cup diced papaya |
| | 1 kiwi fruit |
| | ½ cup puffed rice |
| Lunch | approx. 60 g of the composition mixed in water |
| | 3 rice cakes |
| | ¼ cup Humus |
| | Raw vegetables (Select any non-starchy vegetables you enjoy.) |
| Dinner | Baked potato, topped with |
| | 2 tablespoons toasted sunflower seeds |
| | ½ cup steamed broccoli |
| | ½ cup steamed cauliflower |
| | Bananas, Strawberries and Orange Cream |
| Day 2 | |
| Breakfast | approx. 60 g of the composition mixed in water |
| | 1 cup diced cantaloupe |
| | ½ cup strawberries |
| | ½ cup corn flakes or any other sugar-free cereal except wheat, barley, oat or rye |
| Lunch | approx. 60 g of the composition mixed in water |
| | 2 cups tossed salad with ½ cup garbanzo beans and 1 or 2 tablespoons Italian or oil-based dressing |
| | 1 cup fresh citrus fruits (or 1 orange or grapefruit |
| Dinner | ½ cup steamed brown rice |
| | 2 cups stir-cooked mixed vegetables (Choose from zucchini, carrots cabbage, broccoli, cauliflower, green beans) |
| | 1 cup fresh fruit salad (Select your favorites or choose 1 piece fresh fruit). |
| Day 3 | |
| Breakfast | approx. 60 g of the composition mixed in water |
| | 1 medium pear, diced |
| | 1 cup puffed millet |
| Lunch | approx. 60 g of the composition mixed in water |
| | 1 carrot |
| | 1 stalk celery |

-continued

Week 1

| | |
|---|---|
| | ¼ cup raisins |
| | 4 rice crackers (Look for those that care naturally seasoned with herbs.) |
| Dinner | 2 corn tortillas, heated and topped with |
| | ¾ cup vegetarian refried beans |
| | ½ cup salsa |
| | 1 cup berries |

Day 4

| | |
|---|---|
| Breakfast | approx. 60 g of the composition mixed in water |
| | ½ cup dry cereal (no wheat, oats, barley or rye) |
| | 1 medium banana, sliced |
| Lunch | approx. 60 g of the composition mixed in water |
| | Tossed green salad with |
| | 1 tablespoon Italian dressing |
| | 1 toasted corn tortilla topped with |
| | ½ cup black beans |
| | 2 tablespoons salsa |
| Dinner | 2 cups steamed mixed vegetables (Select from Day 2 dinner suggested vegetables, or choose other non-starchy vegetables.) |
| | 1 cup cooked millet or buckwheat |
| | 1 medium apple |

Day 5

| | |
|---|---|
| Breakfast | approx. 60 g of the composition mixed in water |
| | 1 cup pineapple chunks, fresh or juice-packed (no added sugar) |
| | ½ puffed rice |
| Lunch | approx. 60 g of the composition mixed in water |
| | 2 rice cakes |
| | 2 tablespoons natural peanut butter (Select peanut butter which has not been hydrogenated and has no added sugar.) |
| | 1 piece fresh fruit |
| Dinner | 1 cup vegetarian chilli (or select a natural canned product without additives or preservatives.) |
| | 2 rice cakes |
| | Fresh Vegetable Salad with Peanut Butter Dressing |

Day 6

| | |
|---|---|
| Breakfast | approx. 60 g of the composition mixed in water |
| | Blissful Crepes |
| Lunch | approx. 60 g of the composition mixed in water |
| | 2 rice cakes |
| | ¼ avocado (Mash and use as spread on rice cakes.) |
| Dinner | Quinoa Main Course Salad |
| | Baked Apple with Cashew Topping |

Day 7

| | |
|---|---|
| Breakfast | approx. 60 g of the composition mixed in water |
| | ½ cup cream of rice (prepared with water) |
| | Top cereal with ½ cup freshly grated apple or diced fruit and dust with cinnamon. |
| Lunch | approx. 60 g of the composition mixed in water |
| | 1 apple, quartered |
| | 2 tablespoons tahini (sesame butter) |
| | 4 rice cakes (Spread tahini on apple sections or rice cakes.) |
| Dinner | 1 baked sweet potato, topped with |
| | 2 tablespoons toasted sesame seeds |
| | 1 ½ cups steamed cabbage |
| | 1 cup mixed melon cocktail |

The dietary composition of the example is usually administered for approximately 4 to 16 weeks to a person who is in need of treatment or who can benefit by such treatment with the composition. Usually during this time period a healthy intestinal lining is established or reestablished so that the diseases, conditions or symptoms which necessitated the use of the dietary composition of the invention are cured or eliminated. The beneficial effects of administering the dietary composition of the present invention to persons who are in need of such treatment, or who can benefit by such treatment, are observed and can be numerically demonstrated by changes in the sugar absorption test.

The urinary mannitol and lactulose tests measure the ability of these sugars (mannitol, and lactulose) to penetrate through the intestinal lining. Mannitol is actively absorbed in healthy humans, whereas lactulose is not. Therefore, lactulose can enter the bloodstream, and hence the urine from the blood stream, only through passive absorption. Increased intestinal permeability associated with pathological conditions allows more lactulose to be absorbed and consequent increases are measured in the urine. Malabsorption conditions are indicated by a relative decrease of mannitol in the blood and in the urine. These tests are considered test of "leaky gut" and are conducted substantially as described by M. S. Murphy et al. "Active and Passive Sugar Absorption in Pancreatic Insufficiency" Journal of Pediatric Gastroenterology and Nutrition 3:189–194, 1989 (Raven Press Ltd. New York). The procedure of the test is summarized as follows:

Sugar Absorption Test (Leaky Gut)

The test solution administered contained 5 g lactulose (LAC), 5 g mannitol (MAN), in 100 ml of $H_2O$ (696 mOsm/L). After an overnight fast, the subjects drank 80 ml/m2 of the sugar solution. All urine passed during the next 5 hours was collected in containers with 0.2 ml sodium Merthiolate (10 g/d) as preservative. Fasting was continued for 2 hours after ingesting the test solution, but thereafter the subjects were encouraged to drink fluids in order to increase urine output. An attempt was made to empty the bladder at the end of the collection period. The 5-hour urine volume was recorded and a 20-ml aliquot was stored at −20° C. for subsequent analysis.

Sugars were analyzed by gas-liquid chromatography, using the previously described method of S. C. Fleming "Rapid and Simultaneous Determination of Lactulose and Mannitol in Urine, by HPLC" Clinical Chemistry 1990, 36: 797–799. with inter-and intra-assay coefficients of variation of less than 5%. Marker excretion was expressed at a percentage of the administered dose, and LAC/MAN excretion ratio was calculated. The Fleming et al description for sugar analysis is summarized as follows.

Sample preparation

Depending on the collection volume, urine specimens were diluted between 2.5- and 20-fold with de-ionized water. 1 ml of diluted urine was then mixed with 1 mL of the internal saccharide standards (arabinose 250 mg/L and cellobiose 25 mg/L in deionized water), the mixture was de-salted with 0.5 g of a washed ion-exchange resin (Amberlite IR120 H and IRA400 C1 in mass proportions of 1:1.5), vortex-mixed, and centrifuged. The supernate was filtered through 0.2-um (pore-size) disposable filters (Millipore, Milford, Mass.).

HPLC Analysis

Fifty microliters of the filtrate were injected onto a 250×40 mm Dionex HPIC-AS6 anion-exchange column (Dionex U. K., Camberley, Surrey, U. K.) and eluted with 0.15 mol/L NaOH, at a flow rate of 1 mL/min at 20° C. Detection was by pulsed amperometric detection with a gold working electrode and silver/silver chloride reference electrode with a detection potential of +0.05 V, an oxidation potential of +0.6 V, and a reduction potential of −0.95 V. Quantification was by peak-height analysis and peak-height ratios, with internal standardization.

The attached TABLE 2 shows the results of the sugar absorption test for several patients who were administered the product in 60-gram portions twice daily for the period listed. Positive results can be reflected in several ways as described previously. The mannitol absorption can increase, the lactulose absorption can decrease, and most importantly, the lactulose/mannitol ratio can decrease. As can be seen, consumption of the product described here resulted in each case in improvement in one or several of the sugar absorption test parameters in a period of 12 to 16 weeks.

TABLE 2

SUGAR ABSORPTION TEST

|  | % Lactulose Excretion | % Mannitol Excretion | Ratio of Lactulose/Mannitol |
|---|---|---|---|
| PATIENT #1 |  |  |  |
| Start | 0.5 | 1.0 | 0.5 |
| After 16 weeks | 0.6 | 9.0 | 0.06 |
| PATIENT #2 |  |  |  |
| Start | 0.8 | 9 | 0.09 |
| After 12 weeks | 0.7 | 14 | 0.05 |
| PATIENT #3 |  |  |  |
| Start | 0.3 | 2 | 0.15 |
| After 12 weeks | 1.0 | 17 | 0.06 |

DEMONSTRATION OF REDUCED ANTIGENICITY

The significantly reduced ability of parboiled rice flour, and also of the exemplary product of the present invention which contains parboiled rice flour to induce allergic reactions in humans was demonstrated by the below described Competition ELISA Assay involving a measure of antigen inhibition. The use of antigen inhibition to evaluate relative antigenicity is a well-accepted in the art, see for example Abbas A K Lichtman A H, Pober J S. Cellular and Molecular Immunology; W. A. Saunders, 2ed. 1994: 55–64.

In the Competition ELISA assay the ability of a substance to compete for antibody binding with the parent food, is measured. This assay is generally accepted in the art as an "excellent predictor" of antigenicity (Cordle C T Control of food allergies using protein hydrolysates. Food Tech. 1994; October: 72–76). The general procedure utilized in this assay is described in the above cited publication by Abbas et al. in Cellular and Molecular Immunology. The specifics used in connection with the present invention are described in detail below under the caption "Materials and Methods of the Competition ELISA Assay". A standard rice-extract, referred to as Meta-Rice, was used as a reference source for binding to sera from human patients with known rice sensitivity.

As it is generally understood in the art, the percent of inhibition of the binding by an extract of rice flour to any specific serum indicates the relative antigenicity of that rice flour extract. The greater the inhibition, the more antigenic (allergy inducing) the rice flour is to that serum. In connection with the present invention extracts from three rice flour samples were tested in the assay. The results are shown in TABLE 3. Flour A (obtained from Pacific Grain, Waveland, Calif.) was made from common medium-grain rice. Flour B (obtained from Riviana Foods, Houston, Tex.) was made from common long-grain rice. Flour C (obtained from Riviana Foods, Houston, Tex.) was made from parboiled long-grain rice.

TABLE 4 shows the results of the assay in experiments using medical food products. Specifically, Product 1 in TABLE 4 is a medical food product of the prior art of the same or substantially the same composition as the exemplary food product composition described as the preferred embodiment of this invention, except that Product 1 included rice flour obtained from common rice (Rice Flour A).

In contrast with the prior art product (Product 1), Product 2 is in accordance with the present invention, because it contains only rice flour obtained from parboiled rice (Rice Flour C). Product 2 is the presently preferred embodiment of the invention, and its composition has been described in detail above.

As it can be seen in TABLE 3 and TABLE 4, in these assays when common rice flour is compared to parboiled rice flour, or products made with common rice flour are compared to products made with parboiled rice flour, the percentage of inhibition for parboiled rice is significantly less. This shows that the parboiled rice flour itself and a product made using parboiled rice flour, both are less antigenic than common rice flour or a product made with common rice flour, respectively.

TABLE 3

Competition ELISA Assay - Flour Samples
PERCENT INHIBITION

| SERA | FLOUR A | FLOUR B | FLOUR C |
|---|---|---|---|
| Patient DW | 89% | 89% | 11% |
| Patient 72538 | 92% | — | 39% |

TABLE 4

Competition ELISA Assay - Product Samples
PERCENT INHIBITION

| SERA | PRODUCT 1 | PRODUCT 2 |
|---|---|---|
| Patient 72538 | 89% | 0 |

Materials and Methods of the Competition ELISA Assay

The principle used to evaluate the relative antigenicity of the rice food products was to measure the ability of the rice products to inhibit the reaction between IgG4 antibody in the patient's serum and a standard rice protein extract that has been coated to a microplate well. The reaction was measured using an indirect immunoassay to detect the amount of patient IgG4 which was bound to the reaction well. The enzyme reaction was then detected by adding a suitable colorimetric substrate and measuring the relative absorbance in a microplate spectrophotometer.

Each rice product was tested separately by adding a known amount of the product to a coated microplate well along with the patient's serum. A blank well coating having no inhibitor was used to determine the maximum amount of binding between the patient's IgG4 antibody and the rice extract used to coat the well. If the rice product contains an antigen that is similar to that of the native rice extract, then the maximum reaction is inhibited because the soluble rice product competes with the coated extract for the patient's IgG4 antibody that is present. The soluble IgG4-rice product complexes and unreacted IgG4 antibody are washed away during the procedure and are not measured during the detection step. In contrast, if a rice product has no antigenicity (or has had its antigenicity removed or significantly reduced as part of the processing before testing), then no inhibition occurs because there is not any competitive reaction between the rice product and the coated rice extract for the patient's IgG4 antibody. In this situation, the maximum reaction between the IgG4 antibody and the coated extract occurs and is measured.

For this series of experiments, one rice sensitive patient's serum (DW) was used to test the effect of using different concentrations of the inhibitors to block the reaction with the coating material. The procedure is described below. Unless described otherwise, all reagents were purchased from Sigma Chemical Company, St. Louis, Mo.

Microplate Preparation

The rice extract was diluted 1:100 in a carbonate-bicarbonate buffer (CBC; 0.05 M, pH 9.6). Two hundred microliters of the diluted extract were added to each well of 96 well microplates (RIANEN) and incubated overnight at 4° C. The plates were then washed five times (300 mcl fill, 4 sec soak) using an automated washer (BioRad) using a phosphate-buffered saline (PBS; 0.01 M, pH 7.4). Unreacted binding sites were blocked by adding 200 microliters of 10% horse serum, 1% bovine serum albumin (BSA), diluted in CBC buffer and incubating for 60 minutes at room temperature. The microplates were then rewashed five times as described previously.

Inhibitor Preparation

One gram of each rice product was dissolved in 100 ml of PBS to yield an inhibitor stock solution of 10 mg/ml. The stock solutions were stored at 2–8° C. until use. Subsequent dilutions were prepared as needed using PBS buffer as the diluent.

IgG4 Antibody Procedure

One hundred mcl of inhibitor were added to the appropriate microplate well. PBS was used in some wells to measure the amount of the reaction in the absence of the inhibitor.

One hundred mcl of patient specimen diluted 1:10 in PBS containing 10% horse serum and 1% BSA was then added to each well. The microplates were then allowed to incubate for 2 hours at room temperature on a shaker platform. Following the incubation the plates were washed 5 times as described above.

Two hundred mcl of mouse anti-IgG4 diluted 1:2000 in PBS containing 1% BSA were then added to each well. The microplates were then allowed to incubate for 2 hours at room temperature on a shaker platform. Following the incubation the plates were washed 5 times as described above.

Two hundred mcl of peroxidase-labelled anti-mouse IgG diluted 1:2000 in PBS containing 1% BSA were then added to each well. The microplates were then allowed to incubate for 2 hours at room temperature on a shaker platform. Following the incubation the plates were washed 5 times as described above.

Two hundred mcl of enzyme substrate were then added to each well and the reaction allowed to proceed for 10 minutes at room temperature. The enzyme reaction was then stopped using 100 mcl of 2.5 M $H_2SO_4$.

The net absorbance at 490 nM was then determined using a microplate spectrophotometer (Molecular Devices).

What is claimed is:

1. A composition for treating a harmful condition due to increased gastrointestinal permeability in persons suffering from said condition, the composition comprising:

approximately 38.3 to 46.8 percent by weight of a gluten-free or substantially gluten-free grain protein concentrate which contains approximately 48 to 58 percent by weight of protein;

approximately 14.2 to 21.2 percent by weight of parboiled rice flour;

approximately 16.00 to 24 percent by weight of gluten-free or substantially gluten-free grain syrup solids which contain approximately 70 to 90 percent by weight of high molecular weight dextran;

approximately 1.2 to 1.8 percent by weight of medium chain triglycerides;

approximately 2.7 to 4.0 percent by weight of fructooligosaccharides;

approximately 1.9 to 2.8 percent by weight of inulin;

approximately 0.70 to 1.0 percent by weight of L-glutamine;

a nutritionally acceptable source of panthothenic acid which is equivalent to approximately 0.17 to 0.25 percent by weight of calcium panthothenate;

a nutritionally acceptable source of zinc which is equivalent to approximately 0.05 to 0.08 percent by weight of zinc picolinate;

a nutritionally acceptable source of Vitamin C which is equivalent to approximately 0.18 to 0.26 percent by weight of ascorbic acid, and a nutritionally acceptable source of d-alpha tocopheryl acetate which is substantially equivalent to approximately 0.05 to 0.075 percent by weight of d-alpha tocopheryl acetate.

2. The medical food composition in accordance with claim 1 wherein the parboiled rice flour is from long grain rice.

3. The medical food composition in accordance with claim 2 comprising approximately 17.7 percent by weight of parboiled rice flour.

4. The medical food composition in accordance with claim 1 comprising approximately 1.50 percent by weight of medium chain triglycerides.

5. The medical food composition in accordance with claim 1 comprising approximately 3.37 percent by weight of fructooligosaccharides.

6. The medical food composition in accordance with claim 1 comprising approximately 2.37 percent by weight of inulin.

7. A process for administering to a human being who is in need of treatment for a harmful condition due to increased gastrointestinal permeability, at least twice daily and at least for a duration of approximately 10 days, for the purpose of treating said harmful condition a medical food composition which comprises:

approximately 38.3 to 46.8 percent by weight of a gluten-free or substantially gluten-free grain protein concentrate which contains approximately 48 to 58 percent by weight of protein;

approximately 14.2 to 21.2 percent by weight of parboiled rice flour;

approximately 16.00 to 24 percent by weight of gluten-free or substantially gluten-free grain syrup solids which contain approximately 70 to 90 percent by weight of high molecular weight dextran;

approximately 1.2 to 1.8 percent by weight of medium chain triglycerides;

approximately 2.7 to 4.0 percent by weight of fructooligosaccharides;

approximately 1.9 to 2.8 percent by weight of inulin;

approximately 0.70 to 1.0 percent by weight of L-glutamine;

a nutritionally acceptable source of panthothenic acid which is equivalent to approximately 0.17 to 0.25 percent by weight of calcium panthothenate;

a nutritionally acceptable source of zinc which is equivalent to approximately 0.05 to 0.08 percent by weight of zinc picolinate;

a nutritionally acceptable source of Vitamin C which is equivalent to approximately 0.18 to 0.26 percent by weight of ascorbic acid, and a nutritionally acceptable source of d-alpha tocopheryl acetate which is equivalent to approximately 0.05 to 0.075 percent by weight of d-alpha tocopheryl acetate.

8. The process in accordance with claim 6 wherein the composition is administered in two daily doses of 60 grams.

9. The process in accordance with claim 7 wherein in the composition the grain protein concentrate is rice protein concentrate.

10. The process in accordance with claim 7 wherein in the composition the parboiled grain flour is from long grain rice.

11. The process in accordance with claim 7 wherein in the composition the grain syrup solids are rice syrup solids.

12. The process in accordance with claim 7 wherein in the composition the grain protein concentrate is rice protein concentrate, the parboiled grain flour is from long grain rice and the grain syrup solids are rice syrup solids.

13. The process in accordance with claim 7 wherein in the composition the sources of inulin is chicory.

14. The process in accordance with claim 7 wherein in the composition the sources of fructooligosaccharides is chicory.

15. The process in accordance with claim 7 wherein the composition comprises the following additional components:

approximately 3.2 to 4.8 percent by weight of canola oil;

a nutritionally acceptable source of calcium which is substantially equivalent to approximately 1.3 to 1.96 percent by weight of calcium citrate;

a nutritionally acceptable source of flavor which is substantially equivalent to approximately 1.2 to 1.8 percent by weight of natural Vanilla Flavor # 1018;

a nutritionally acceptable source of magnesium which is substantially equivalent to approximately 1.03 to 1.55 percent by weight of magnesium citrate;

a nutritionally acceptable buffering agent which is substantially equivalent in its buffering capacity to approximately 0.72 to 1.08 percent by weight of dibasic potassium phosphate;

approximately 0.0025 to 0.004 percent by weight of β-carotene or a carotinoid mixture which is substantially equivalent to said quantity of β-carotene;

a nutritionally acceptable buffering agent which is substantially equivalent in its buffering capacity to approximately 0.16 to 0.25 percent by weight of dicalcium phosphate;

approximately 0.06 to 0.09 percent by weight of L-lysine hydrochloride, L-lysine or a nutritionally acceptable salt of L-lysine in a quantity substantially equivalent to said quantity of L-lysine hydrochloride;

a nutritionally acceptable source of chromium containing chromium ions in the trivalent or hexavalent form, and which is substantially equivalent to approximately 0.00010 to 0.00016 percent by weight of chromium;

approximately 0.05 to 0.07 percent by weight of L-threonine;

a nutritionally acceptable source of selenium which is substantially equivalent in selenium content to approximately 0.00006 to 0.00010 percent by weight of selenium;

a nutritionally acceptable salt of iron which is equivalent in iron content to approximately 0.015 to 0.023 percent by weight ferrous fumarate;

approximately 0.0107 to 0.016 percent by weight niacinamide or niacin in substantially equivalent quantity to said quantity of niacinamide;

a nutritionally acceptable salt of divalent or pentavalent manganese ions which is substantially equivalent in manganese content to approximately 0.0241 to 0.0361 percent by weight of manganese gluconate;

a nutritionally acceptable salt of copper which is equivalent in copper content to approximately 0.005 to 0.007 percent by weight of copper gluconate;

approximately 0.008 to 0.012 percent by weight of Vitamin A solution containing $5 \times 10^5$ I.U. of Vitamin A per gram;

a nutritionally acceptable salt of pyridoxine which is equivalent to approximately 0.001 to 0.002 percent by weight of pyridoxine hydrochloride;

approximately 0.0009 to 0.0013 percent by weight of riboflavin;

a nutritionally acceptable salt of thiamine which is substantially equivalent to approximately 0.0008 to 0.0012 percent by weight of thiamine hydrochloride;

a nutritionally acceptable form of vitamin D which is substantially equivalent in its vitamin D activity to approximately 0.0016 to 0.0024 percent by weight of vitamin D3 solution containing $1 \times 10^5$ I.U. of Vitamin D3 per gram;

approximately 0.00024 to 0.0004 percent by weight of folic acid;

biotin or a nutritionally acceptable salt of biotin which is substantially equivalent to approximately 0.0001 to 0.0003 percent by weight of biotin;

approximately 0.00010 to 0.00019 percent by weight of Vitamin K;

approximately $3.2 \times 10^{-6}$ to $5.0 \times 10^{-6}$ percent by weight of cyanocobalamin;

a nutritionally acceptable molybdenum salt in a quantity which is substantially equivalent to approximately 0.00007 to 0.00010 percent by weight of molybdenum;

approximately 0.007 to 0.01 percent by weight of N-acetylcysteine;

approximately 0.007 to 0.01 percent by weight of glutathione, and approximately 0.009 to 0.013 percent by weight of L-cysteine hydrochloride.

16. The process in accordance with claim 7 wherein the composition is administered twice daily in conjunction with a substantially vegetarian diet.

* * * * *